(12) United States Patent
Lovell

(10) Patent No.: US 8,877,061 B2
(45) Date of Patent: Nov. 4, 2014

(54) DIALYZER WITH DUAL SAFETY VALVES

(76) Inventor: Gloria Lovell, Altadena, CA (US)

( * ) Notice: Subject to any disclaimer, the term of this patent is extended or adjusted under 35 U.S.C. 154(b) by 942 days.

(21) Appl. No.: 12/613,755

(22) Filed: Nov. 6, 2009

(65) Prior Publication Data

US 2011/0108482 A1 May 12, 2011

(51) Int. Cl.
*B01D 61/00* (2006.01)
*B01D 11/00* (2006.01)
*B01D 63/00* (2006.01)
*B01D 21/24* (2006.01)
*A61M 1/16* (2006.01)

(52) U.S. Cl.
CPC .............. *A61M 1/16* (2013.01); *A61M 1/1621* (2014.02)
USPC ................... 210/645; 210/321.6; 210/321.71; 210/97; 210/117

(58) Field of Classification Search
CPC ...... B01D 61/28; B01D 61/243; B01D 61/32; B01D 2313/243; B01D 61/24; B01D 61/00
USPC ........... 210/321.71, 645, 97, 117, 321.6, 634; 220/660, 661, 725
See application file for complete search history.

(56) References Cited

U.S. PATENT DOCUMENTS

| | | | |
|---|---|---|---|
| 3,323,541 A * | 6/1967 | Schneider, Jr. et al. | 137/312 |
| 3,483,990 A * | 12/1969 | Sternberg et al. | 210/321.78 |
| 4,230,579 A * | 10/1980 | Bray et al. | 210/101 |
| 4,834,888 A | 5/1989 | Polaschegg | |
| 5,580,460 A | 12/1996 | Polaschegg | |
| 5,863,421 A * | 1/1999 | Peter et al. | 210/134 |
| 5,882,516 A | 3/1999 | Gross et al. | |
| 6,274,034 B1 * | 8/2001 | Nikaido et al. | 210/97 |
| 6,558,537 B1 * | 5/2003 | Herrington et al. | 210/192 |
| 6,582,604 B2 * | 6/2003 | Nikaido et al. | 210/636 |
| 8,029,456 B2 * | 10/2011 | Fung | 604/15 |
| 8,109,893 B2 * | 2/2012 | Lande | 604/6.07 |
| 2002/0104800 A1 * | 8/2002 | Collins et al. | 210/646 |
| 2004/0068219 A1 * | 4/2004 | Summerton et al. | 604/5.01 |
| 2006/0113249 A1 * | 6/2006 | Childers et al. | 210/645 |
| 2009/0113781 A1 * | 5/2009 | Myers, IV | 43/3 |
| 2009/0326457 A1 * | 12/2009 | O'Connor | 604/151 |
| 2010/0192686 A1 * | 8/2010 | Kamen et al. | 73/290 R |
| 2011/0259371 A1 * | 10/2011 | Schlaeper et al. | 134/22.13 |
| 2012/0018378 A1 * | 1/2012 | Kelly et al. | 210/646 |
| 2012/0106289 A1 * | 5/2012 | Wilt et al. | 366/162.1 |
| 2013/0020237 A1 * | 1/2013 | Wilt et al. | 210/85 |

* cited by examiner

Primary Examiner — Ana Fortuna
(74) Attorney, Agent, or Firm — Fox Rothschild LLP

(57) ABSTRACT

An apparatus for purifying body fluid with solution including a casing having first and second input and output ports and dual safety or check valves monolithically formed with the casing that operate in conjunction with a dialysis machine or other apparatus used in hemodialysis is disclosed. The dual safety valves are configured at the input and output ports of a dialyzer such that the apparatus allows body fluid to move in one direction. This configuration prevents the reverse flow of body fluid back into the apparatus. A method for purifying body fluid with solution using an apparatus is further disclosed.

22 Claims, 2 Drawing Sheets

DIALYZER WITH DUAL SAFETY VALVES

BACKGROUND OF THE INVENTION

This invention relates to an apparatus, system and/or method for hemodialysis and, more particularly, to a dialyzer with dual safety valves for stopping dialysis solution from reversing and leaking through input and output ports.

Artificial kidney systems usually include a dialyzer and a dialysis machine which controls the operation of the dialyzer. The dialyzer is used to treat a patient's blood so as to remove water and waste products therefrom. Such dialyzers include a semi-permeable membrane which separates the blood and the dialysis solution flowing through the dialyzer. Waste product removal occurs by mass transfer through the membrane, and water removal occurs by ultrafiltration through the membrane. When a dialysis session is finished, it is necessary to remove the dialyzer and discard thereof. The problem is that there are no suitable means available to close off the inlet and outlet of the dialyzer, thus exposing the patient and caregiver to waste products as they remove the dialyzer from the dialysis machine.

SUMMARY OF THE INVENTION

Given the above deficiencies of prior art, a need remains for a dialyzer with novel assembly to shield the caregiver and patient from dialysis hazards. The present invention satisfies such a need by providing an assembly that is convenient and easy to use, is durable in design, and ensures the well being of the caregiver and patient by greatly reducing incidences of exposure to germs, bacteria and blood-borne pathogens so often associated with administering dialysis treatment. The assembly is not only limited to protecting the caregiver from exposure to harmful bio-hazardous waste, by preventing the dialyzer from spilling or leaking fluids, but use of the present invention also ensures that hospital flooring remains clean and dry during the dialysis procedure. As such, caregivers and patients alike are spared the dangers of slipping and falling which can easily occur when traversing a slippery floor.

The present invention is directed to a method, device, apparatus, or system. An apparatus embodiment in accordance with the present invention includes a dialyzer casing having a dialysate inlet and outlet with check valves disposed adjacent to the inlet and outlet, allowing the dialysate to flow only in one direction. The casing also has a fluid inlet and outlet for body fluid to be treated flowing therethrough. A first check valve is arranged between the dialysate inlet and a dialysate entry line leading to the dialyzer casing, while a second check valve is arranged between the dialysate outlet and a dialysate exit line departing from the dialyzer casing.

The apparatus can further include a first and second cover secured to the casing at the fluid inlet and outlet. The first and second covers can be sealed to the casing by a sealing compound.

Preferably, the apparatus further includes a third check valve disposed between the fluid inlet and a fluid entry line leading to the dialyzer casing; and a fourth check valve disposed between the fluid outlet and a fluid exit line departing from the dialyzer casing. As with the first and second check valves, the third and fourth check valves also restrict flow in only one direction.

In one aspect, the check valves described above can be formed with the inlets and outlets of the dialyzer casing. The check valves also may include a loop of elastomer therein for sealing to other objects.

In another aspect, the casing includes a semi-permeable membrane installed therein to filter the body fluid from the solution. The semi-permeable membrane can be made of cellulose or synthetic. The casing can be made of plastic, glass, or acrylic fiber, etc. The solution used within the apparatus typically includes mineral ions.

DETAILED DESCRIPTION OF THE PREFERRED EMBODIMENT(S)

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art.

The assembly of this invention is referred to generally in the figures and is intended to provide a dialyzer with dual safety valves. It should be understood that the assembly may be used to provide dual valve filters in many different types of applications and should not be limited in use to only dialysis.

Figure 1:
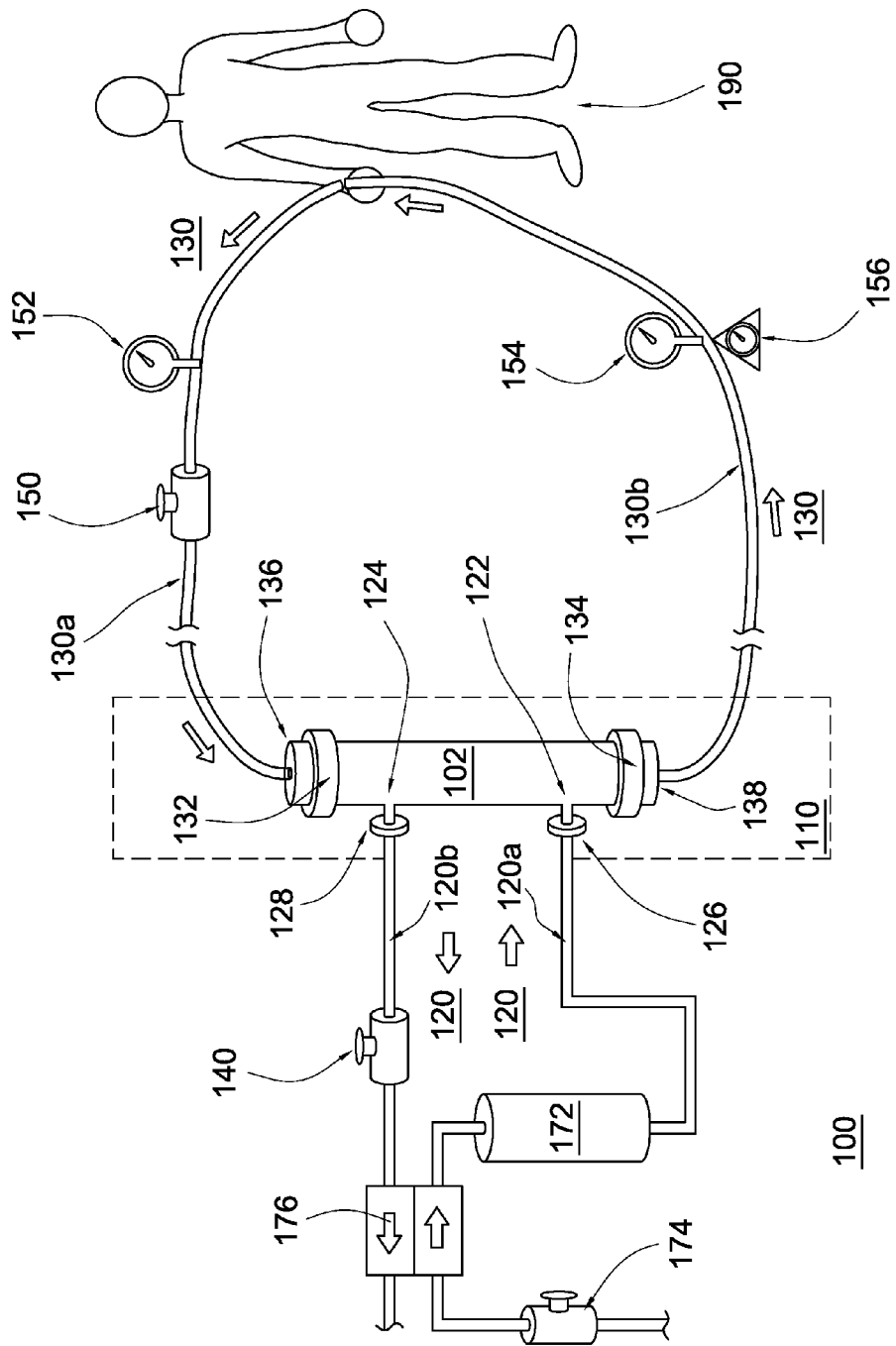
FIG. 1 illustrates a hemodialysis apparatus with the present invention embodied therein.

FIG. 1 depicts a hemodialysis apparatus 100 with a dialyzer assembly 110 embodying the present invention therein. The dialyzer assembly 110 includes a casing 102 that is suitably sized and shaped to work in conjunction with the hemodialysis apparatus 100 to pump blood from a patient's body and clean wastes from the pumped blood. Specifically, the casing 102 provides a space to tentatively retain blood for mixing with dialysis solution (dialysate) to purify when the dialysis procedure is taking place. The dialyzer casing 102 has four openings to receive and send forth the dialysis solution and blood: the input port 122 and output 124 for the dialysis solution to pass through, and the input port 132 and output port 134 for blood to pass through.

During hemodialysis operation, the dialysis solution is fed to the casing 102 of the dialysis assembly 110 through dialysate path identified by reference numeral 120. The dialysate path 120 consists of the following members: (1) an dialysate entry line 120a; (2) an input port 122 of the casing 102 that communicates with the dialysate entry line 120a; (3) space within the casing 102 that the dialysis solution flows through; (4) an output port 124 of the casing 102 that communicates with an dialysate exit line 120b; and (5) the dialysate exit line 120b. As noted above, a vital goal for designing the dialysate path 120 is to prevent backflow of dialysis impurities into a patient 190 through the dialysate path 120. Accordingly, the present invention integrates with the casing 102 check valves identified as reference numerals 126 and 128 that can restrict the dialysis solution to flow in only one direction. Specifically, the check valve 126 disposed between the input port 122 and entry line 120a can cut off fluid reversing from opening of the casing 102, thereby ensuring clean supply of the dialysis solution to the dialyzer casing 102. Similarly, the check valve 128, being disposed between the output port 124 and dialysate exit line 120b, can isolate the discharged, contaminated fluid from the blood that is being cleansed within the casing 102. Because the check valves 126 and 128 can halt dialysate reversing, leaking and spilling is prevented at the input port 122 and output port 124.

Referring to FIG. 1, body fluid such as blood to be treated by the hemodialysis apparatus 100 is drawn from the patient 190 and then carried into the dialyzer assembly 110. An extracorporeal circuit 130 that the body fluid flows through consists of the following members: (1) an extracorporeal entry line 130a; (2) an input port 132 of the casing 102 that communicates with the extracorporeal entry line 130a; (3) flowing path of the body fluid within the casing 102; (4) an output port 134 of the casing 102 that communicates with an extracorporeal exit line 130b; and (5) the extracorporeal exit line 130b.

Check valves can be also installed on the extracorporeal circuit 130 to prevent reversing of the body fluid or blood, reflecting one embodiment of the present invention. As shown in FIG. 1, the check valves identified as reference numerals 136 and 138 are respectively disposed between the extracorporeal entry line 130a and the dialyzer casing 102, and between the extracorporeal exit line 130b and the dialyzer casing 102. They serve to separate the patient's cleansed blood from the contaminated.

To maintain a continuing yet steady flow of the fluid circulating in the hemodialysis apparatus 100, pumps are typically used with the dialyzer assembly 110. By way of example, a dialysate pump identified as reference numeral 140 in FIG. 1 is connected to the downstream of the dialysis path 120 (the dialysate exit line 120b) to effectuate flow of the dialysis solution. In addition, a blood pump identified as reference numeral 150 is positioned in the upstream of the extracorporeal circuit 130 (the extracorporeal entry line 130a) to ensure continuous flow of the blood that is withdrawn from the patient. Other pumps (not shown) may also be installed in the hemodialysis apparatus 100 for various purposes, such as withdrawing extra liquid from the dialysate exit line 120b for discharge, and providing continuous feed of heparin to prevent blood clotting.

The remaining portions of the hemodialysis apparatus 100 correspond to commercially known systems, which typically include the following primary components as shown in FIG. 1: a dialyzing fluid filter 172, a dialysate pump 140, an ultrafiltration pump 174, a balancing chamber 176, an arterial pressure monitor 152, a venous pressure monitor, and an air trap and detector 156.

Figure 2:
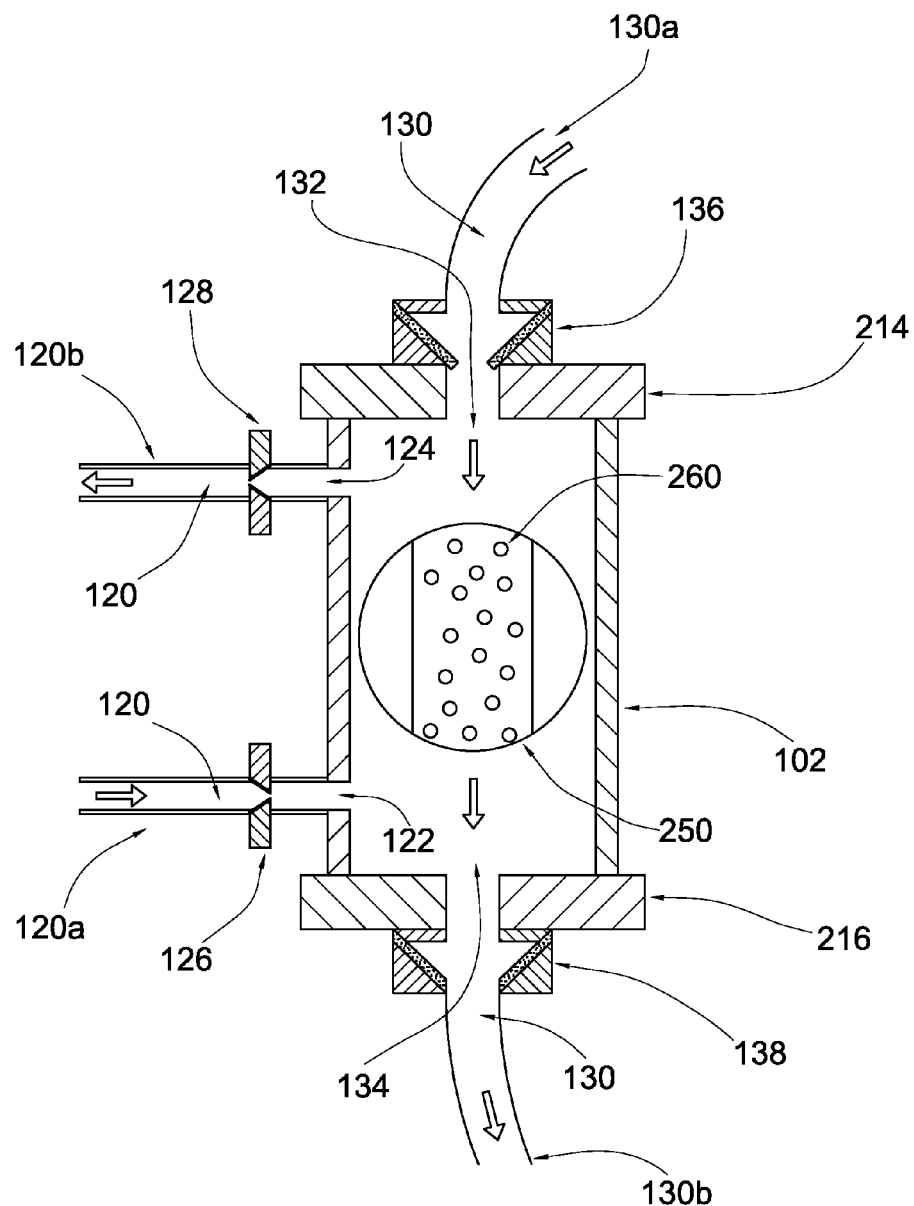
FIG. 2 provides a cross-sectional view of a dialyzer in accordance with the present invention.

FIG. 2 illustrates a cross-sectional view 200 of an exemplary embodiment of the dialyzer assembly 110 with reference to FIG. 1. Because FIG. 2 substantially corresponds to portions of FIG. 1, the counter parts are denoted by the identical reference numerals.

Referring to FIG. 2, the dialyzer casing 102 of the dialyzer assembly 110, in many commercial variants, is cylindrical and elongated. The casing shell can be made of plastic, glass, acrylic fiber or other suitable materials that do not react with dialysis solution contained therewithin. The dialyzer casing 102 can be sealed at the input port 132 and output port 134 by caps 214 and 216, as delineated in FIG. 2. Sealing compounds can be used to seal off the dialyzer casing 102 with the caps 214 and 216 to the extremity.

Inside the dialyzer casing 102 is anchored a plurality of micro fibers (not shown) through which blood is passed and filtered. The walls of the micro fibers are composed of semipermeable membrane, a portion of which is enlarged and identified as reference numeral 250 in FIG. 2. Because the semi-permeable membrane 250 consists of pores 260 too small to let blood cells pass through, it can effectively filter waste products from blood while the dialysis solution flows through the dialyzer casing 102. In commercial applications, the semi-permeable membrane 250 may come with different pore sizes and made of cellulose or synthetic materials.

In operating the hemodialysis apparatus 100, dialysis solution is pumped around the micro fibers, flowing in the opposite direction to blood flow in the extracorporeal circuit 130. Counter-current flow increases the efficiency of the hemodialysis. Fluid removal (ultrafiltration) is achieved by causing free water and some dissolved solutes to move across the membrane 250 by pressure gradient. The motion allows wastes and extra fluids to pass from the blood into the solution, which then carries them away. The dialysis solution employed to carry the waste product is typically a sterilized solution of mineral ions, which can diffuse urea, potassium, and phosphate, etc.

The check valves 126 and 128 used in the dialyzer assembly 110 each include two sides in the body, one for fluid to enter only and the other one for fluid to exit only. When the upstream at the entering side exceeds a minimal pressure, the check valves 126 and 128 are forced to open both sides, thereby permitting the flow to pass through the valve body. The downstream of fluid, however, is blocked by the valve's exit side from backflow once past the valve body. The sensitivity of the check valves 126 and 128 are tuned to a level that can smoothly pass fluid flow for the hemodialysis operation. The check valves 126 and 128 can be made of any suitable materials that are bio-compatible.

Preferably, the check valves 126 and 128 are monolithically formed with the casing 102 at the input port 122 and the output port 124 so that possible reversing flow is halted immediately where the casing 102 is communicating therefrom. Accordingly, when the dialyzer assembly 110 is being removed from the hemodialysis apparatus 100, residue of dialysis solution or blood that remains in the dialysate entry line 120a and dialysate exit line 120b can be controlled at a minimum. In addition, as the check valves 126 and 128 are built with the dialyzer casing 102, least modification will be required of the dialysate entry line 120a and dialysate exit line 120b to accommodate the dialyzer assembly 110. Where the whole body of the check valves 126 and 128 is wholly incorporated within the dialyzer casing 102, not only does the dialysis assembly 110 provide benefits of unity, but the casing 102 can also serve as a structure to protect the valves from collision.

In other implementations, the check valves 126 and 128 are coupled to the casing 102, immediately connected to the input port 122 and output port 124, respectively. It is also possible that the check valves 126 and 128 are placed adjacent to the casing 102 but not directly connected to the input and output ports. As a result, there exists a section between the input port 122 and check valve 126, as well as between the output port 124 and check valve 128. While the purpose of the present invention to obstruct backflow can still be realized in such an assembly, this arrangement would cause some waste of dialysate at least in the section between the input port 122 and the dialysate entry line 120a.

Materials such as glue compounds, various rubber or plastic types, and/or metals may be used to ensure sealing of the connection spots. O-ring, toric joint, or the like may also be mounted to the check valves 126 and 128 or the dialysate entry line 120a and dialysate exit line 120b to reinforce sealing.

Like the check valves 126 and 128, the check valves 136 and 138 can be monolithically formed with the casing 102 at the input port 132 and the output port 134. Accordingly, the blood residue remaining in the extracorporeal entry line 130a and extracorporeal exit line 130b would not fall out upon removal of the dialyzer assembly 110 from the hemodialysis apparatus 100. Where the check valves 136 and 138 are wholly incorporated within the dialyzer casing 102, the dialysis assembly 110 furnishes benefits such as installation simplicity and protection for the valves.

In various implementations, the check valves 136 and 138 are positioned adjacent to the dialyzer casing 102, while being either directly or indirectly connected to the input port 132 and output port 134. The dialysis assembly 110 with the check valves 136 and 138 adjoining the input and output ports, however, is a more effective arrangement to minimize blood residue that remains in the extracorporeal circuit 130 between the ports and valves. As such, least amount of blood would have to be discarded from the extracorporeal circuit 130 upon completion of the dialysis procedure.

As with the check valves 126 and 128 employed in the dialysate path 120, the check valves 136 and 138 for the extracorporeal circuit 130 can be made of any suitable materials that are bio-compatible. The check valves 136 and 138 can be sealed or secured to the ports and extracorporeal lines by like materials or mechanism as described above regarding the check valves 126 and 128.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto. It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention. In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed is:

1. An apparatus for purifying body fluid with solution comprising:
   a casing having:
      a first input port for receiving the solution via a solution entry line;
      a first output port for sending forth the solution via a solution exit line;
      a second input port for receiving the body fluid via a fluid entry line;
      a second output port for sending forth the body fluid via a fluid exit line; and
      a semi-permeable membrane installed therein for filtering the body fluid from the solution;
   a first check valve disposed adjacent to the first input port for connecting to the solution entry line and restricting the solution to only enter the casing, wherein the first check valve is monolithically formed with the casing at the first input port; and
   a second check valve disposed adjacent to the first output port for connecting to the solution exit line and restricting the solution to only exit the casing, wherein the second check valve is monolithically formed with the casing at the first output port.

2. The apparatus of claim 1, wherein the first and second check valves each include a loop of elastomer therein for sealing.

3. The apparatus of claim 1, further comprising:
   a first cover securing to the casing at the second input port; and
   a second cover securing to the casing at the second output port; wherein the first and second covers are sealed to the casing with a sealing compound.

4. The apparatus of claim 1, wherein the semi-permeable membrane is made of one of the following materials:
   cellulose; and
   synthetic.

5. The apparatus of claim 1, wherein the solution includes mineral ions.

6. The apparatus of claim 1, further comprising:
   a third check valve disposed between the second input port and the fluid entry line for restricting the body fluid to only enter the casing; and
   a fourth check valve disposed between the second output port and the fluid exit line for restricting the body fluid to only exit the casing.

7. The apparatus of claim 6, wherein the third check valve is formed with the second input port and the fourth check valve is formed with the second output port.

8. The apparatus of claim 6, wherein the third and fourth check valves each include a loop of elastomer therein for sealing.

9. The apparatus of claim 1, wherein the casing is made of one of the following materials:
   plastic;
   glass, and
   acrylic fiber.

10. The apparatus of claim 1, further comprising:
    a dialysate pump for connecting into the solution exit line to move flow of the solution.

11. The apparatus of claim 1, further comprising:
    a blood pump for connecting into the fluid entry line to move flow of the body fluid.

12. A method for purifying body fluid with solution using an apparatus, the apparatus comprising:
    a casing having:
       a first input port for receiving the solution via a solution entry line;
       a first output port for sending forth the solution via a solution exit line;
       a second input port for receiving the body fluid via a fluid entry line;
       a second output port for sending forth the body fluid via a fluid exit line; and
       a semi-permeable membrane installed therein for filtering the body fluid from the solution;
    a first check valve disposed adjacent to the first input port for connecting to the solution entry line and restricting the solution to only enter the casing, wherein the first check valve is monolithically formed with the casing at the first input port; and
    a second check valve disposed adjacent to the first output port for connecting to the solution exit line and restricting the solution to only exit the casing, wherein the second check valve is monolithically formed with the casing at the first output port.

13. The method of claim 12, wherein the first and second check valves each include a loop of elastomer therein for sealing.

14. The method of claim 12, wherein the apparatus further comprises:
   a first cover securing to the casing at the second input port; and
   a second cover securing to the casing at the second output port; wherein the first and second covers are sealed to the casing with a sealing compound.

15. The method of claim 12, wherein the semi-permeable membrane is made of one of the following materials:
   cellulose; and
   synthetic.

16. The method of claim 12, wherein the solution includes mineral ions.

17. The method of claim 12, wherein the apparatus further comprises:
   a third check valve disposed between the second input port and the fluid entry line for restricting the body fluid in one direction to only enter the casing; and
   a fourth check valve disposed between the second output port and the fluid exit line for restricting the body fluid in one direction to only exit the casing.

18. The method of claim 17, wherein the third check valve is formed with the second input port and the fourth check valve is formed with the second output port.

19. The method of claim 17, wherein the third and fourth check valves each include a loop of elastomer therein for sealing.

20. The method of claim 12, wherein the casing is made of one of the following materials:
   plastic;
   glass, and
   acrylic fiber.

21. The method of claim 12, wherein the apparatus further comprises:
   a dialysate pump for connecting into the solution exit line to move flow of the solution.

22. The method of claim 12, wherein the apparatus further comprises:
   a blood pump for connecting into the fluid entry line to move flow of the body fluid.

* * * * *